United States Patent
Awaad et al.

(10) Patent No.: US 9,233,096 B2
(45) Date of Patent: Jan. 12, 2016

(54) METHOD OF PROVIDING AN ANTI-ULCER TREATMENT WITH EXTRACTS AND ISOLATED FLAVONOIDS FROM EUPHORBIA CUNEATA

(71) Applicant: King Saud University, Riyadh (SA)

(72) Inventors: Amani S. Awaad, Riyadh (SA); Reham Moustafa El-Meligy, Riyadh (SA)

(73) Assignee: King Saud University, Riyadh (SA)

(*) Notice: Subject to any disclaimer, the term of this patent is extended or adjusted under 35 U.S.C. 154(b) by 0 days.

(21) Appl. No.: 14/296,711

(22) Filed: Jun. 5, 2014

(65) Prior Publication Data
US 2014/0288016 A1 Sep. 25, 2014

Related U.S. Application Data

(62) Division of application No. 13/544,044, filed on Jul. 9, 2012, now abandoned.

(30) Foreign Application Priority Data

Sep. 22, 2011 (EP) .................................... 11182357

(51) Int. Cl.
| | |
|---|---|
| A61K 31/352 | (2006.01) |
| A61K 36/47 | (2006.01) |
| A61K 31/7048 | (2006.01) |
| A61K 31/353 | (2006.01) |
| C07D 311/40 | (2006.01) |
| C07H 17/07 | (2006.01) |

(52) U.S. Cl.
CPC ............. *A61K 31/352* (2013.01); *A61K 31/353* (2013.01); *A61K 31/7048* (2013.01); *A61K 36/47* (2013.01); *C07D 311/40* (2013.01); *C07H 17/07* (2013.01); *A61K 2236/30* (2013.01)

(58) Field of Classification Search
CPC .............................. A61K 31/352; A61K 36/47
See application file for complete search history.

(56) References Cited

U.S. PATENT DOCUMENTS

| 5,650,433 A | 7/1997 | Watanabe et al. |
| 7,033,606 B1 | 4/2006 | Besse et al. |
| 7,553,501 B2 | 6/2009 | Olalde Rangel |
| 2006/0198905 A1* | 9/2006 | Jain et al. ....................... 424/725 |

FOREIGN PATENT DOCUMENTS

| CN | 1872082 | 12/2006 | |
| EP | 2003-342190 | 12/2003 | |
| RU | 2406520 C2 * | 12/2010 | ............. A61K 36/48 |
| WO | 2007/149902 | 12/2007 | |
| WO | 2008/048044 | 4/2008 | |

OTHER PUBLICATIONS

English machine translation of RU 2406520, http://worldwide.espacenet.com/, accessed online on Jul. 23, 2015.*
Akbar et al., Australian Journal of Medical Herbalism, 2011, 23(2), p. 76-87, published Jun. 22, 2011.*
Nasrollahzadeh et al., Chemistry of Natural Compounds, 2011, 47(3), p. 434-435, dated Jul. 27, 2011.*
Lee et al., J. Food Sci. Nutr., 2005, 10, p. 103-110.*
Mota Kelly Samara De Lira et al: "Flavonoids with gastroprotective activity", Molecules (Basel, Switzerland), vol. 14. No. 3, 2009, pp. 979-1012.
Bahar Ahmed, Tawfeq A Al-Howiriny, Jaber S Mossa & K E H El Tahir: "Isolation, antihypertensive activity and structure activity relationship of flavonoids from three medicinal plants", Indian Journal of Chemistry, vol. 44B, Feb. 2005, pp. 400-404.
De Barros et al: "Effect of Brazilian green propolis on experimental gastric ulcers in rats", Journal of Ethnopharmacology. vol. 110. No. 3, Mar. 13, 2007, pp. 567-571.
Bafna P A et al: "Anti-ulcer and anti-oxidant activity of Pepticare, a herbomineral formulation", Phytomedicine, vol. 12. No. 4, Apr. 20, 2005, pp. 264-270.
Falcao et al: "Plants of the American continent with antiulcer activity", Phytomedicine, vol. 15. No. 1-2, Dec. 22, 2007, pp. 132-146.
Hari Babu T et al: "Gastroprotective flavonoid constituents from Oroxylum indicum Vent", Bioorganic & Medicinal Chemistry Letters. vol. 20, No. 1, Jan. 1, 2010, pp. 117-120.
EP 11 18 2357; European Search Report dated Jan. 24, 2012.
Awaad et al., Antioxidant Natural Plant; Recent Progress in Medicinal Plants, 2010, Studium Press Llc, vol. 27, pp. 1-35.
Aganov et al., 13C NMR Spectra of Organic Peroxides; Bull. Acad. Sci. USSR, 1982, 31(2), pp. 247-250.

* cited by examiner

*Primary Examiner* — Jonathan S Lau
(74) *Attorney, Agent, or Firm* — Renner, Otto, Boisselle & Sklar, LLP

(57) ABSTRACT

The present invention relates to methods of isolating flavonoids from *Euphorbia cuneata*, and a pharmaceutical composition comprising the flavonoids or the extracts or both of them for a use as anti-ulcer agent. The present invention further relates to a method of providing an anti-ulcer treatment to an animal in need thereof comprising administering to the animal a compound selected from 4'-methoxy-luteolin-7-O-rhamnoglucoside and aromadendrin. A method of providing an anti-ulcer treatment to an animal in need thereof comprising administering to the animal a compound selected from 4'-methoxy-luteolin-7-O-rhamnoglucoside and aromadendrin, in which the compound(s) are isolated from *Euphorbia cuneata*.

7 Claims, No Drawings

METHOD OF PROVIDING AN ANTI-ULCER TREATMENT WITH EXTRACTS AND ISOLATED FLAVONOIDS FROM *EUPHORBIA CUNEATA*

CROSS-REFERENCE TO RELATED APPLICATIONS

The present application is a division of and claims priority under 35 U.S.C. §§120 and 121 to U.S. application Ser. No. 13/544,044, filed 9 Jul. 2012, now abandoned, which in turn claims priority under 35 U.S.C. §119 to European Application No. 11182357.1, filed 22 Sep. 2011, the entirety of each of which is hereby incorporated herein by reference. The present application is also related to U.S. application Ser. No. 14/296,698, filed 5 Jun. 2014, which in turn claims priority under 35 U.S.C. §119 to European Application No. 11182357.1, filed, 22 Sep. 2011. U.S. application Ser. No. 14/296,698, filed 5 Jun. 2014, is hereby incorporated herein by reference.

The present invention relates to flavonoids isolated from *Euphorbia cuneata*, a method for isolation thereof, extracts from *Euphorbia cuneata* and a pharmaceutical composition comprising the flavonoids or the extracts or both of them.

INTRODUCTION

The use of plants as a therapeutic agent is well known from the previous decades, however, when man developed synthesized drugs led to many side effects. To minimise or avoid the side effects of synthesized drugs man return back to nature in order to discover natural curing agents. Euphorbiaceae is one of the largest plant families (321 genera and 7950 species) and most of its species contain a milky or colored latex. The latex is poisonous in some species and many of them contain irritant and pesticidal substances. The genus *Euphorbia* constitutes the largest number of this family. It comprises 700 species of trees, shrubs or herbs with acrid milky juice.

This genus is of great importance due to its various phytochemical constituents as phenolic compounds, terpenoids, tannins. In addition it was well known due to its variable medicinal uses, such as acetyl choline-like action with muscarinic and nicotinic activities on isolated ileum of rabbit, spasmolytic, diuretic, increase of capillary strength, antileukemic, anti-inflammatory analgesic and decrease of the release of prostaglandin.

Rantidine is disclosed in U.S. Pat. No. 4,128,658 to be an effective $H_2$ antagonist and therefore suitable for the treatment of gastric ulcer by inhibiting the production of stomach acid.

In the publication of Min et al., Autonomic & Autocoid Pharmacol., 2005, 25, 85-91, the use of apigenin in anti-ulcer treatment has been described.

Flavonoids are known to be responsible for the antiulcerogenic activities of many plants. Naringin was reported to have antiulcerogenic activity as disclosed by example in the publications of Martin et al. Pharmacology, 1994, 49, 144-150 and Motilva et al. J. Pharm. Pharmacol. 1993, 46, 91-94.

It is an object of the present invention to provide novel and effective anti-ulcer agents obtained from natural materials.

It is also an object of the present invention to provide a flexible method for the isolation of antiulcerogenic active compounds from natural materials.

The first object is achieved by an extract from *Euphorbia cuneata*, selected from one of the first or second extracts, obtained by the following steps:
a) providing a plant material derived from *Euphorbia cuneata*,
b) drying the plant material,
c) extracting the plant material using a first organic solvent to obtain a first extract,
d) concentrating the first extract,
e) suspending the concentrated first extract obtained in step d) in water,
f) extracting the watery phase obtained in step e) using a second organic solvent to obtain a second extract, and
g) concentrating the second extract.
for a use as an anti-ulcer agent.

Thereby, the plant material consists of the aerial parts of *Euphorbia cuneata*.

Preferably, drying is carried out in air.

Even preferred, drying is carried out in the dark.

In one embodiment, the first extraction is carried out in a Soxhlet apparatus.

In another preferred embodiment, the first organic solvent is ethanol.

Preferably, the concentration of the first and/or second extract is carried out under reduced pressure at a temperature below 35° C.

In a preferred embodiment, the second organic solvent is diethyl ether, chloroform, ethyl acetate or n-butanol.

More preferred, the second organic solvent is ethyl acetate or n-butanol.

The first object of the present invention is also achieved by a compound selected from 4'-O-methoxy-luteolin-7-O-rhamnoglucoside and aromadendrin, for use as an anti-ulcer agent.

The second object is achieved by a method to isolate a compound selected from the group consisting of 4'-O-methoxy-luteolin-7-O-rhamnoglucoside and/or aromadendrin from *Euphorbia cuneata*, comprising the following steps:
h) first purification of the concentrated second extract obtained in step g) by column chromatography,
i) second purification of a residual obtained in step h) by preparative thin layer chromatography, and
j) third purification of a residual obtained in step i) by gel filtration, to obtain one or more of the compounds.

In one embodiment, the stationary phase used for the column chromatography is silica gel.

In another embodiment, the eluent used for the column chromatography is ethyl acetate or methanol or mixtures thereof.

Preferably, a cross-linked dextran gel is used for gel filtration.

The object of the present invention is also achieved by a pharmaceutical composition comprising 4'-O-methoxy-luteolin-7-O-rhamnoglucoside and/or aromadendrin according to claim 1 and/or an extract from *Euphorbia cuneata*, according to claim 2.

Preferably, the pharmaceutical composition is formulated for oral administration.

Surprisingly, it was found out that the compounds and the extracts of the present invention solve the problem by exhibiting a similar or in some cases even higher antiulcerogenic activity compared to the substances used in the prior art.

Also, it was found out that the substances and extracts of the present invention can be easily obtained from the natural material *Euphorbia cuneata* by an easy and flexible purification method.

The total extracts possessed antiulcerogenic activity at different doses. Flavonoidal compounds were isolated and identified as: aromadendrin and 4'-O-methoxy-luteolin-7-O-rhamnoglucoside, all of them featuring antiulcerogenic activity. The antioxidative activity of this plant and its isolated compounds may explain the antiulcerogenic properties. No side effects were reported on liver and kidney functions.

The antiulcerogenic activity of the total alcohol extract of *Euphorbia cuneata* was studied using ethanol-induced ulcer model at doses of 125, 250 and 500 mg/kg. The active compounds were isolated and identified using IR, $^{13}$C-NMR and $^1$HNMR and the antiulcerogenic activity of the isolated compounds at the dose of 100 mg/kg was also evaluated. The antioxidant properties to the total alcohol extract and the isolated compounds were evaluated using DPPH radical scavenging activity test. The liver and kidney functions were studied.

The term "pharmaceutical composition", as used herein, is intended to comprise the extracts or the isolated substances of the present invention. Also considered is a pharmaceutical composition comprising at least one pharmaceutical active extract of the present invention and/or at least one of the isolated compounds of the present invention and corresponding salts thereof.

The pharmaceutical composition can be, for example, in a liquid form, e.g. a solution, syrup, elixir, emulsion and suspension, or in a solid form, e.g. a capsule, caplet, tablet, pill, powder and suppository. Granules or semi-solid forms and gelcaps are also considered. In case that the pharmaceutical composition is a liquid or a powder, dosage unit optionally is to be measured, e.g. in the dosage unit of a teaspoonful. In addition to one of the extracts or the isolated compounds, the pharmaceutical composition can comprise, for example, flavouring agents sweeteners, dyes stabilizers, colouring agents, diluents, suspending agents, granulating agents, lubricants, binders and disintegrating agents. A tablet, for example, can be coated. All of the formulations mentioned can be intended for immediate-release, timed-release and sustained release.

All components of the pharmaceutical composition have to be pharmaceutically acceptable. The term "pharmaceutically acceptable" means at least non-toxic. The therapeutically active compounds should preferably be present in the above-mentioned pharmaceutical composition in a concentration of about 0.1 to 99.5, preferably of about 0.5 to 95% by weight of the total mixture.

It will be understood by those skilled in the art that various modifications and substituents may be made to the invention as described above without departing from the spirit and scope of the invention. Accordingly, it is understood that the present invention have been described by a way of illustration and not limitation.

EXAMPLES

Example 1

Recovery of Plant Materials

The aerial parts of E. cuneata (Euphorbiaceae) were collected during flowering stage in 2010, from Desert of Saudi Arabia. The sample was kindly identified by Dr. M. Gebali, botanist and by comparison with the published plant description (El-Gohary, 2004). Plant material was air-dried in shade, reduced to fine powder, packed in tightly closed containers and stored for phytochemical and biological studies.

Example 2

Phytochemical Screening

Powdered samples of the aerial parts of Euphorbia cuneata, Vahl were subjected to preliminary phytochemical screening according to the published methods (Awaad, 2009).

Example 3

Extraction

One kilogram of the air dried powder of E. cuneata (aerial parts) was extracted by percolation in 90% ethanol at room temperature for two days and subsequent filtration. The residue was re-percolated again. The combined ethanol extracts were concentrated under reduced pressure at a temperature not exceeding 35° C. to yield a dry extract (290 g). Water (400 ml) was added and the resultant mixture successively extracted with diethyl ether, chloroform, ethyl acetate, and n-butanol respectively. Each extract was dried over anhydrous sodium sulphate, and concentrated under reduced pressure at a temperature not exceeding 35° C. to yield dry extracts (5.5, 6, 18.5 and 60 g) respectively. All extracts were tested for their antiulcerogenic and antioxidant activities. The ethyl acetate and n-butanol extracts were the most effective extracts.

Example 4

Isolation

TLC of the extracts obtained in Example 3 featured the same pattern of spots when each extract was chromatographed on silica gel G using the solvent systems (a); ethyl acetate: methanol:water (30:5:4) & (b); chloroform-methanol (95:5). Visualization was achieved by UV lamp and/or an aluminum chloride spray reagent. Therefore both extracts were combined (78 g) and a portion applied to a silica gel column which was eluted gradually with ethyl acetate and methanol. Different fractions containing phenolic compounds were isolated. These were each subjected to preparative thin layer chromatography using solvent system (a and b). Bands corresponding to each compounds were separately extracted with methanol, concentrated and for final purification each one was submitted to a column of Sephadex LH-20 eluted with methanol:water 1:1, giving compounds 1 and 2.

Example 5

Identification of Isolated Compounds

As flavonoids were isolated and identified: aromadendrin (2,3-dihydro-kaempferol) and 4'-O-methoxy-luteolin-7-O-rhamnoglucoside. Identification was carried out by TLC chromatography, UV spectroscopy, EI-MS, $^1$H NMR and $^{13}$C NMR.

Apparatus:

Melting points were determined on a Kofler hot-stage apparatus and are uncorrected, mass spectra (Electrospray negative ion) sample dissolved in acetonitrile on a Micromass Quattro spectrometer. $^1$H and $^{13}$C NMR spectra, using external electronic referencing through the deuterium resonance frequency of the solvent, were determined at 600.17 or 150.91 MHz respectively with a JEOL ECA600 NMR spectrometer fitted with an auto-tune 5 mm X/H probe. Carbon atom types were established in the $^{13}$C NMR spectrum by employing a combination of broad-band proton-decoupled and DEPT (90 and 135) experiments. [$^1J_{C-H}$] and $^2J_{C-H}$ and $^3J_{C-H}$] $^1$H—$^{13}$C correlations were established by using HMQC and HMBC pulse sequences respectively. $^1$H—$^1$H correlations were determined by double quantum filtered COSY. Pye Unicam pu 8800 spectrophotometer for UV spectral analysis. the amino acid analyzer (Eppendorf-LC 3000). Shimadzu—IR-435 infrared spectrophotometer.

Aromadendrin (2,3-dihydro-kaempferol) 1: yellowish white crystals, m.p. 221-223° C., soluble in methanol, $R_f$ value=0.614 (b). UV λ max, (nm), (MeOH) 290, 295(sh), (NaOMe), 245, 325, (NaOAc) 316, 327, (NaOAc/$H_3BO_3$) 311, 336, $AlCl_3$, 294, 380, ($AlCl_3$/HCl), 295, 378. $^1$H-NMR (methanol-D3), 5.0 (1H, d, J=2.0 Hz, H-2), 4.5 (1H, dd, J=5.5, 1.7 Hz) 3, 5.82 (1H, d, J=2.0 Hz) 8, 5.87 (1H, d, J=2.0 Hz) 6, 6.7 (2H, d, J=8.5 Hz) 3', 5', 7.2 (2H, d, J=8.5 Hz) 2', 6'. $^{13}$C-NMR (DMSO-d6) 83.4 (C-2), 71.9 (C-3), 198.4 (C-4), 163.8 (C-5), 96.5 (C-6), 167.3 (C-7), 95.5 (C-8), 163.1 (C-9), 100.9 (C-10), 128.0 (C-1'), 130.0 (C-2'), 115.4 (C-3'), 158.2 (C-4'), 115.4 (C-5'), 130.0 (C-6').

4'-O-methoxy-luteolin-7-O-rhamnoglucoside 2: Was obtained as yellow crystals, soluble in methanol, $R_f$ value=0.59 (b) Ultra-violet, λ max, (nm), (MeOH), 271.323, 336, NaOMe, 275, 400, NaOAc, 273, 338, NaOAc/$H_3BO_3$, 272, 336, $AlCl_3$, 272, 336, $AlCl_3$/HCl, 274, 360. $^1$H-NMR in methanol-D3, 0.9 (3H, s) Protons of methyl group of rhamnose, 3.2-3.6 (m) Sugar protons, 4.0 (3H, s) Methoxy protons, 5.3 (1H, s) Anomeric proton, 5.4 (1H, s) Anomeric proton, 6.10 (1H, d, 3.4 Hz) 8, 6.30 (1H, s) 3, 6.38 (1H, d, 3.4 Hz 6), 6.8 (1H, d, J=13.8 Hz) 5', 7.4 (1H, q) 6', 7. (H, d, J=3.5 Hz) 2'. $^{13}$C-NMR spectra: in DMSO-d6, 157.0 C2, 101.7 C3, 177.7 C4, 156.98 C5, 94.7 C6, 161.6 C7, 94.3 C8, 149.9 C9, 104.3 C10, 121.5 C1', 113.7 C2', 133.4 C3', 147.3 C4', 115.7 C5', 122.7 C6', 101.4 C1", 74.7 C2", 76.8 C3", 70.8 C4", 76.4 C5", 63.5 C6", 99.3 C1''', 71.0 C2''', 72.2 C3''', 73.0 C4''', 68.8 C5''', 18.2 C6'''.

Example 6

Pharmacological Study

Preparation of the plant extract: Dried aerial parts of *E. cuneata* (300 g) were extracted in a Soxhlet apparatus with ethanol 95%. The ethanol extract was completely dried under vacuum, weighed and the residue was used in testing. The dried plant extract was freshly suspended in distilled water just before administration by the aid of Tween 80.

Determination of Median Lethal Dose ($LD_{50}$):

LD50 of the tested extract was determined. For this purpose, albino mice (20-22 g) were divided into groups of 5 animals each. Several doses (50-4000 mg/kg) at equal intervals were given orally to mice. Animals were kept under observation for 24 hour.

Antiulcerogenic Activity:

Male Wister rats (180-200 g) were used. They were kept under good hygienic conditions and fed on standard diet and watered ad libitum. Animals were divided into groups each of 6 rats and starved for 48 h before use to ensure an empty stomach. To avoid dehydration during the period of fasting, rats were supplied with sucrose (BDH) 8% (w/v) solution in NaCl (BDH) 0.2% (w/v), which was removed one hour before experimentation. The $1^{st}$ group was kept as a normal control, while the $2^{nd}$ one was kept as a positive control. Groups $3^{rd}$ to $5^{th}$ received the alcohol extract of *E. cuneata* in doses of 125, 250 and 500 mg/kg orally. Groups $6^{th}$ to $9^{th}$ received diethyl ether, chloroform, ethyl acetate, and n-butanol extracts respectively at dose of 125 mg/kg orally, other groups ($10^{th}$ to $12^{th}$) received the isolated compounds (1-2) respectively at dose of 100 mg/kg orally. The last three groups of rats were given ranitidine, apigenin and naringin orally as reference drugs in a dose of 100 mg/kg.

Two doses were given in the first day at 08:00 and 16:00 clock; a third dose was given on the second day 1.5 h before induction of gastric ulceration. All rats except the normal control were given ethanol (Merck) 50% (v/v) (in distilled water) in a dose of 10 ml/kg orally to induce gastric ulceration. Normal control rats received equivolumes of distilled water only at the same time intervals. One hour after ethanol administration, all rats were killed by an overdose of chloroform and the stomachs were rapidly removed, opened along their greater curvature and gently rinsed under running tap water. Lesions in the glandular part of the stomach were measured under an illuminated magnifying microscope (10×). Long lesions were counted and their lengths were measured. Petechial lesions were counted, and then each five petechial lesions were taken as 1 mm of ulcer. To calculate the ulcer index (mm), the sum of the total length of long ulcers and petechial lesions in each group of rats was divided by its number. The curative ratio was determined according to the formula:

$$\text{Curative ratio} = \frac{(\text{Control ulcer index}) - (\text{Test ulcer index})}{(\text{Control ulcer index})} \times 100$$

The results obtained were statistically analyzed using "t" test.

Effect on Liver and Kidney Functions

Mature rats of 150-180 gm b. wt. were divided into 2 equal groups 10 rats each. The $1^{st}$ group was left as a control, while the $2^{nd}$ group was orally given the plant extracts in a dose (500 mg/kg) for 15 days. Blood samples were collected from the orbital plexus of rats, 6 hr after medication. Samples were left to clot at room temperature for 20 min. The obtained sera were collected and used to determine the activity of (AST) aspirate aminotransferase and (ALT) alanine aminotransferase. Levels of urea, creatinine were also estimated.

Pharmacological Activity

Determination of median Lethal Dose ($LD_{50}$): The total alcohol extract *E. cuneata* did not produce any behavioral changes and mortality in mice in doses up to 4000 mg/kg. Therefore, the tested plant can be categorized as highly safe since substances possessing LD50 higher than 50 mg/kg are non toxic.

Antiulcerogenic Activity:

The present results showed that the plant extract has an antiulcerogenic activity at doses of 250 and 500 mg/kg which is similar to that of ranitidine or waringin, while the low dose (125 mg/kg) was less effective than ranitidine at dose of (100 mg/kg). The ethyl acetate and n-butanol extracts were the most effective extracts; from which the effective compounds were isolated. The isolated compounds at a dose of 100 mg/kg were effective as antiulcerogenic, the compound 4'-O-methoxy-luteolin-7-O-rhamnoglucoside was the most effective (it was even more effective than ranitidine), followed by aromadendrin which were as effective as naringin, apigenin and ranitidine (100 mg/kg) (Table 1).

Liver and Kidney Functions:

Both liver and kidney functions were not affected as there is no significant difference between control and test groups in all experiments, at the 0.05 level of probability (Table 2).

TABLE 1

The antiulcerogenic effect of extracts and isolated compounds from *E. cuneata*.

| Treatment (Dose mg/kg) | No. of ulcers | Curative ratio |
|---|---|---|
| Control | 17.020 ± 1.115 | 0 |
| Total alcohol extract (125) | 12.000 ± 1.390* | 29.49 |
| Total alcohol extract (250) | 5.543 ± 0.992** | 67.43 |
| Total alcohol extract (500) | 3.975 ± 0.882** | 76.65 |
| Diethyl ether extract (125) | 10.000 ± 0.147* | 41.25 |
| Chloroform extract (125) | 11.968 ± 0.532* | 29.68 |
| Ethyl acetate extract (125) | 7.067 ± 0.122* | 58.48 |
| n-butanol extract (125) | 8.667 ± 0.572* | 49.08 |
| Rantidine (100) | 3.200 ± 0.800** | 81.20 |
| Naringin (100) | 3.167 ± 0.872** | 81.40 |
| Aromadendrin (100) | 3.558 ± 0.640** | 79.10 |
| Apigenin (100) | 4.122 ± 0.432** | 75.78 |
| 4'-O-methoxy-luteolin-7-O-rhamnoglucoside (100) | 2.003 ± 0.072*** | 88.23 |

Values are mean ± SD, (n = 6);
*P < 0.05 compared with control group.

TABLE 2

Effect of fifteen daily administrations of alcohol extract on kidney and liver functions.

| Treatment | Liver functions | | Kidney functions | |
| --- | --- | --- | --- | --- |
| | ALT (U/I) | AST (U/I) | Urea (mg/dl) | Creatinine (mg/dl) |
| Control | 10.800 ± 0.583 | 13.000 ± 0.707 | 50.812 ± 3.568 | 0.970 ± 0.016 |
| Total ethanol extract | 11.600 ± 3.999 | 13.800 ± 1.019 | 66.556 ± 5.208 | 1.078 ± 0.045 |

Values are mean ± SD, (n = 10);
*P < 0.05 compared with control group.

The invention claimed is:

1. A method of providing an anti-ulcer treatment to an animal in need thereof comprising administering to the animal an effective amount of aromadendrin.

2. The method according to claim 1 wherein the aromadendrin is contained in a pharmaceutical composition.

3. The method according to claim 2, wherein the pharmaceutical composition is formulated for oral administration.

4. A method of providing an anti-ulcer treatment to an animal in need thereof comprising administering to the animal compounds an effective amount of aromadendrin obtained by a method to isolate aromadendrin from *Euphorbia cuneata*, comprising the following steps:
   a) providing a plant material derived from *Euphorbia cuneata*,
   b) drying the plant material,
   c) extracting the plant material using a first organic solvent to obtain a first extract,
   d) concentrating the first extract,
   e) suspending the concentrated first extract obtained in step d) in water,
   f) extracting the watery phase obtained in step e) using a second organic solvent to obtain a second extract,
   g) concentrating the second extract,
   h) a first purification of the concentrated second extract obtained in step g) by column chromatography,
   i) a second purification of a residual obtained in step h) by preparative thin layer chromatography, and
   j) a third purification of a residual obtained in step i) by gel filtration, to obtain the aromadendrin.

5. The method according to claim 4, wherein the stationary phase used for the column chromatography is silica gel.

6. The method according claim 4, wherein the eluent used for the column chromatography is ethyl acetate or methanol or mixtures thereof.

7. The method according to claim 4, wherein a cross-linked dextran gel is used for the gel filtration.

* * * * *